(12) United States Patent
Heuft

(10) Patent No.: US 6,199,679 B1
(45) Date of Patent: Mar. 13, 2001

(54) DEVICE AND PROCESS FOR INSPECTION OF OBJECTS, PARTICULARLY BEVERAGE BOTTLES

(75) Inventor: Bernhard Heuft, Burgbrohl (DE)

(73) Assignee: Heuft Systemtechnik GmbH, Burgbrohl (DE)

( * ) Notice: Subject to any disclaimer, the term of this patent is extended or adjusted under 35 U.S.C. 154(b) by 0 days.

(21) Appl. No.: 09/101,983

(22) PCT Filed: Jan. 20, 1997

(86) PCT No.: PCT/EP97/00244

§ 371 Date: Jul. 20, 1998

§ 102(e) Date: Jul. 20, 1998

(87) PCT Pub. No.: WO97/26091

PCT Pub. Date: Jul. 24, 1997

(30) Foreign Application Priority Data

Jan. 19, 1996 (DE) .......................................... 296 00 902 U

(51) Int. Cl.[7] .................................................. B65G 47/24
(52) U.S. Cl. ........................ 198/415; 198/346.2; 209/545
(58) Field of Search ................................. 198/415, 346.2; 209/545, 540

(56) References Cited

U.S. PATENT DOCUMENTS

| 2,636,602 | 4/1953 | Stoate et al. | 209/111 |
| 5,020,908 | 6/1991 | Hermann | 356/239 |

FOREIGN PATENT DOCUMENTS

| 1431365 | 12/1975 | (DE) | B65G/47/68 |
| 3532068 | 8/1989 | (DE) | G01N/21/90 |
| 4207835 | 9/1993 | (DE) | B07C/5/34 |
| 9310623 | 12/1993 | (DE) | B07C/5/36 |
| 4330796 | 3/1995 | (DE) | B65G/47/68 |
| 9402229 | 4/1995 | (DE) | B65B/47/68 |
| 0295371 | 12/1988 | (EP) | G01N/21/90 |
| 0324285 | 7/1989 | (EP) | G01N/21/90 |
| 0415154 | 3/1991 | (EP) | B07C/5/34 |
| 62-16920 | 1/1987 | (JP) | B65G/47/31 |
| PCT/EP96/05193 | 11/1996 | (WO) | |

*Primary Examiner*—Joseph E. Valenza
*Assistant Examiner*—Joe Dillon, Jr.
(74) *Attorney, Agent, or Firm*—Gardner, Carton & Douglas

(57) ABSTRACT

In order to inspect objects (10), particularly drinks bottles, these are transported on two conveyors (12, 14), which exhibit a mutual lateral separation and run at different speeds, so that the objects (10) rotate about their vertical axis. Within the distance separating the conveyors (12, 14) a bottom checking installation (30, 32) is provided. A rail (16) for guiding the objects (10) can be arranged, stretching in the direction of transport above the first, slower-running conveyor (12), in such a way that the objects (10) on the first conveyor (12) stand on the edge strip between the rail (16) and the edge of the first conveyor (12), and the width of this edge strip amounts to up to about ⅓ of the diameter of the objects.

15 Claims, 3 Drawing Sheets

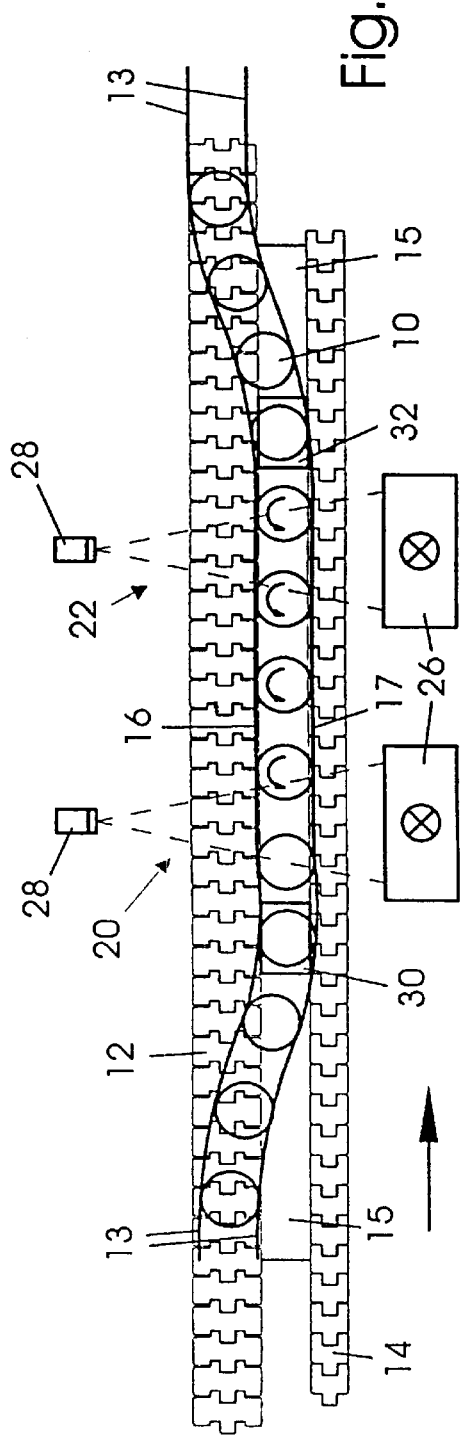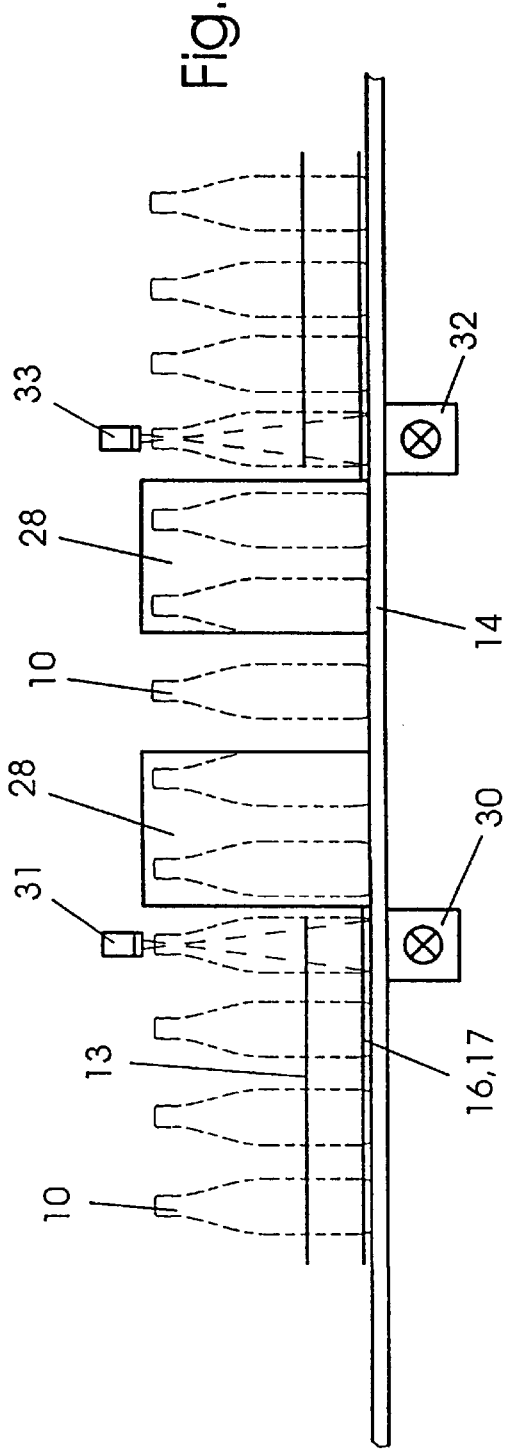

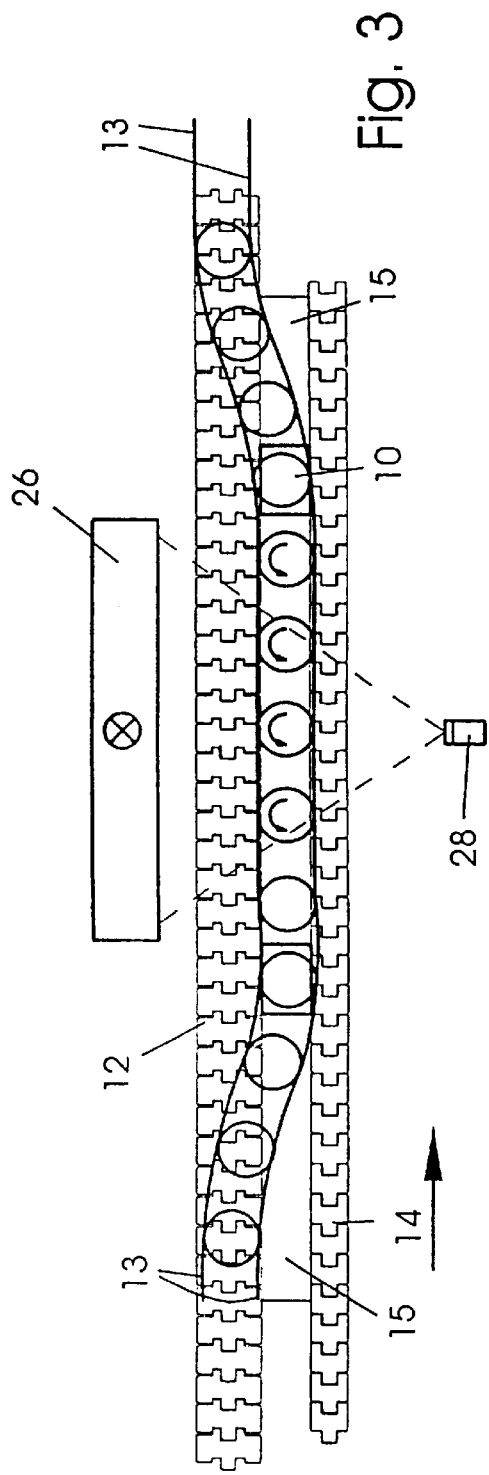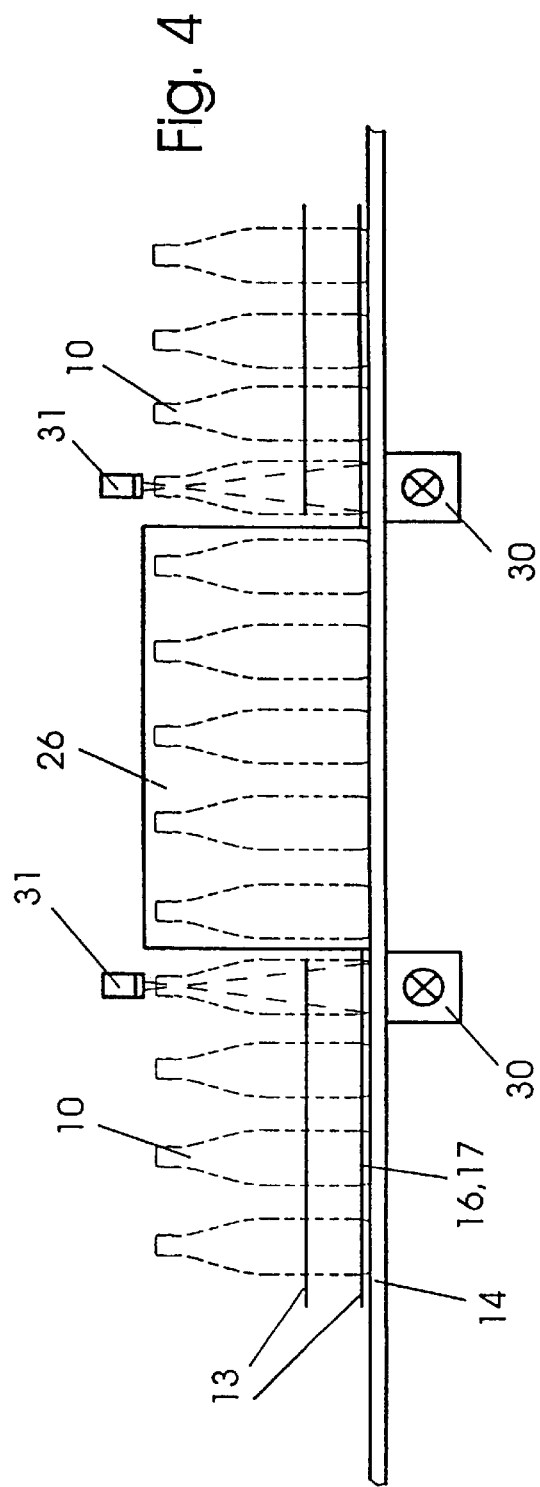

DEVICE AND PROCESS FOR INSPECTION OF OBJECTS, PARTICULARLY BEVERAGE BOTTLES

FIELD OF THE INVENTION

The invention relates to a device and a method for inspecting objects, particularly empty drinks bottles. The device includes a conveyor installation, which features a number of conveyors running at different speeds with an essentially horizontal conveyor surface for conveying and at the same time rotating the objects.

SCOPE OF THE PRIOR ART

In an inspection device of this type, which is known from DE-A-35 32 068, the conveyor installation consists of a total of four conveyor belts running at different speeds, the belts being arranged next to each other with no separation. Because of the different speeds of the conveyor belts, the objects standing on them are made to rotate, in such a way that a single side wall checking installation is sufficient to inspect every object over its entire circumference.

An inspection device is known from EP-A-0 415 154, in which the objects are inspected by two side wall checking installations, and are rotated by 90° about their vertical axis on the way between the two side wall checking installations. The objects are rotated by virtue of the fact that, between the two side wall checking installations, they are held by their sides by conveyor belts which are running at different speeds. In this region the objects are not supported on their underside, and, that being so, a bottom inspection can be carried out in this region.

SUMMARY OF THE INVENTION

The object of the invention is to improve the universal applicability of devices and methods of this type for various objects, particularly empty bottles of various diameters.

This object is achieved, according to the invention, in that the conveyor installation is formed by two conveyors arranged with a lateral separation, in which a bottom checking installation, which features a radiation source and a recognition installation, is provided within the separation between the conveyors.

This solution is noteworthy due to its mechanical simplicity and robustness.

A rail is preferably arranged stretching in the direction of transport over the first, slower-running conveyor in such a way that the objects can roll or slide along the rail. The separation between the rail and the edge of the conveyor and the separation between the two conveyors is preferably chosen to be such that the objects stand with a larger part of their bottom surface on the first, slower conveyor than on the second, faster one. The width of the region of the slower conveyor on which the objects stand can be up to about ⅓ of the radius of the objects. The second, faster conveyor preferably has a top surface with a friction coating, so that the friction between the under surface of the objects on the faster conveyor is greater than on the slower conveyor. For particularly unstable objects, the rails can also be constructed so as to run along with the objects, in the form of a synchronously running belt or a conveyor, which makes use of vertically projecting engagement lugs on its chain links.

A side wall checking installation is preferably provided, featuring a light source and a recognition installation, between which the objects are conveyed through by the conveyor installation. In order, furthermore, to minimise the space required for the inspection equipment, further inspection installations, such as checking of the mouth and the screw top, and checking for soap suds, are preferably carried out simultaneously during the crossover phase or during the rotation phase, e.g. simultaneously with the side wall checking. This is possible because the movement can be frozen by stroboscopic illumination or shutter cameras, and the rotation of the bottles, for example, therefore causes no disturbance.

It has been shown that the objects stand up securely enough although they are only supported on lateral edge portions of their under surface. In particular, the speed at which the objects rotate about their vertical axis is very steady.

The inspection device is arranged on a conveyor, on which the objects, for example empty bottles, are transported. This conveyor represents the first conveyor of the inspection installation. The second conveyor is arranged parallel to it, separated by a distance of about ⅔ to ¾ of the diameter of the objects and parallel to the first conveyor. At the intake end of the inspection device, the objects are shifted, by a rail running at an angle over the first conveyor, laterally towards the second conveyor, so that they stand with edge regions of their under surface on both conveyors. While being shifted laterally, they continue to be supported by crossover plates which bridge the gap between the first conveyor and the second conveyor. The crossover plates are generally restricted to the region in which the objects are being shifted from the first conveyor in the direction of the second conveyor. As soon as the objects are standing on both conveyors, no further supplementary support is required for the objects, so the crossover plates do not stretch into this region. If needs be, in the case of very unsteady objects, for example drinks bottles with a small under surface, a guide rail can be provided, arranged, between the two conveyors, for example, at the height of the conveyor levels or slightly lower, which prevents the objects toppling over in the direction of travel or against the direction of travel.

The bottom checking is preferably carried out twice over an interval within which the objects are rotated by 90° or 270°. In that way the entire bottom region can be inspected despite the lateral portions being masked by the conveyors. Furthermore, the bottom inspection can be carried out several times after rotation by appropriate subdivisions of 360°, for example in three sections after rotation by 60° on each occasion or 60°+180°.

The bottom inspection can also be carried out in two increments following as closely as possible on one another, and with no actual defined rotation of the objects between the two increments. In this case, both increments of the bottom inspection are carried out in the region of the crossover plates arranged at the intake end or at the outlet end of the inspection device. To that end, the crossover plate consists of transparent material, for example glass or scratch-resistant plastic. Two bottom-checking installations are arranged under the transparent crossover plate, staggered along the direction of transport. The first bottom-checking installation is arranged to be at the place where the objects have about 60% of their under surface standing on the crossover plate, while they are being moved along with the remaining 40% of their under surface still on the first conveyor. The second bottom checking installation is arranged downstream at the place where at most about 40% of the object is standing on the second conveyor, while about 60% of its under surface is still located on the transparent crossover plate. By means of the first and second bottom checking installations, about 60% of the bottom can be inspected at any one time, such that the two 60% regions together amount to the entire bottom surface of the objects, even allowing for a slight rotation of the objects. Next the objects are again shifted back transversely to the direction of transport by means of a rail, so that they now come to stand on both conveyors, and the rotation of the objects, for side wall inspection, for example, can be brought into action. In this form of the invention, the objects are shifted laterally by the rail far enough towards the second conveyor for them to leave the first conveyor completely and stand only on the crossover plate and the second conveyor. By means of a rail acting on the other side, the objects are shifted back again sufficiently far from there towards the first conveyor, after the second bottom inspection, for them to stand with edge portions of their under surface on both conveyors. While being shifted back in this way, the objects are once again supported on the crossover plate, which in this form of the invention is extended accordingly. The side wall checking can again be carried out as explained in the first embodiment of the bottom checking, after rotation of the objects through 90°, or the field of view of the recognition installation, for example a CCD camera, can be so chosen that the objects rotate through about 220 to 270° within this field of view, so that the entire circumference can be inspected.

BRIEF DESCRIPTION OF THE FIGURES

Exemplary embodiments of the invention will be explained below by means of the drawings. These show:

FIGS. 1 and 2 in plan view and in side view respectively, an embodiment of the device for inspecting objects, in which both the bottom inspection as well as the side wall inspection are repeated after a rotation of 90°;

FIGS. 3 and 4 in plan view and in side view respectively, an embodiment in which the side wall inspection is carried out continuously within a region in which the objects rotate by about 220°, while the bottom inspection is repeated after a rotation of 90°, and FIG. 5 in plan view, an embodiment in which the bottom inspection is carried out in two increments within the region of the crossover plate arranged at the intake end.

DETAILED DESCRIPTION OF THE PREFERRED EMBODIMENT

Figure 5:
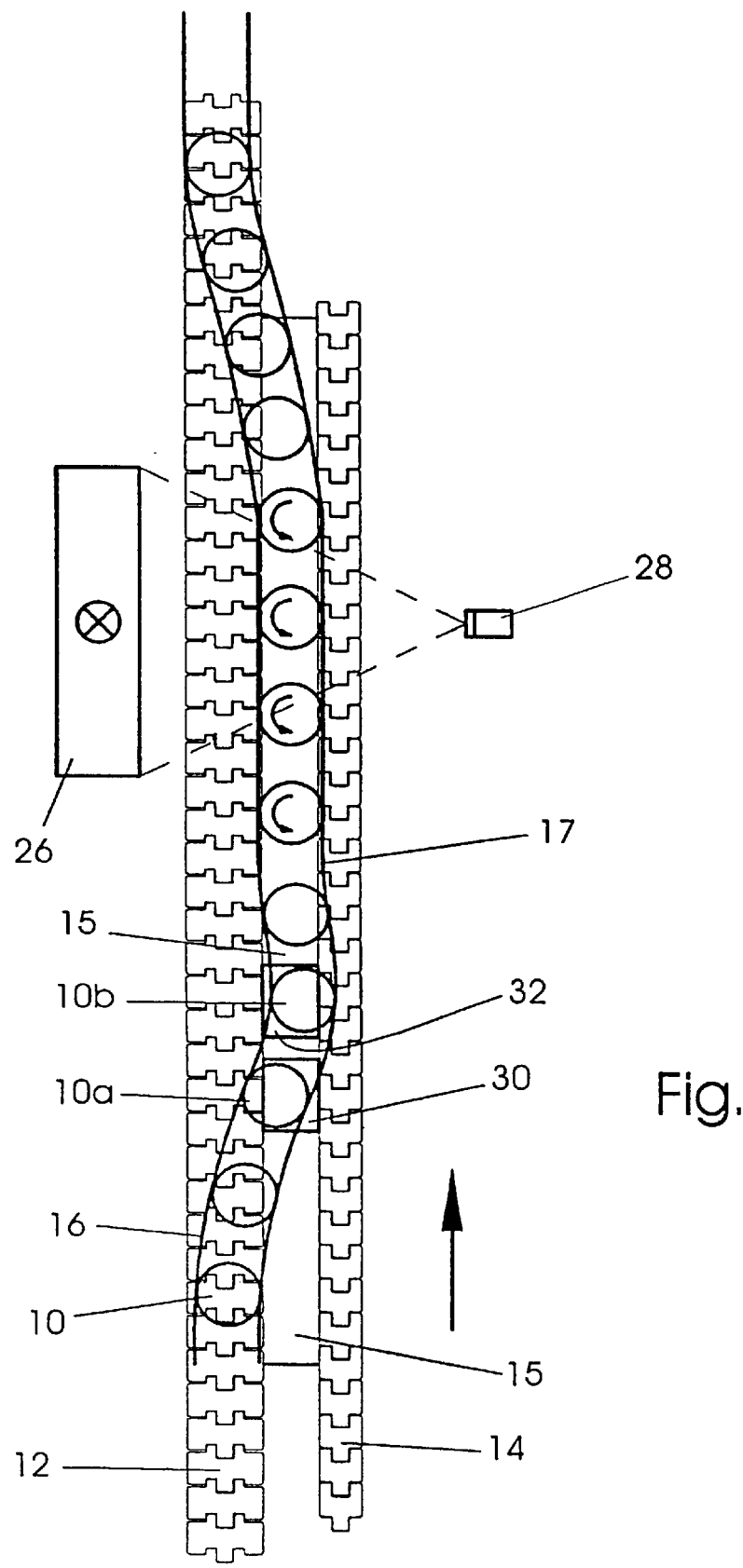

FIGS. 1 and 2 show a device for inspecting empty bottles 10, which are the objects to be inspected in this case. The conveyor installation is composed of a first conveyor 12 and a second conveyor 14. The empty bottles 10 are conveyed on the first conveyor 12 to the inspection device. Between the two conveyors 12, 14, there is a separation of about ⅔ to ¾ of the diameter of the empty bottles 10. The first and second conveyors 12, 14 can be the usual chain link conveyors or conveyor belts. Before the inspection device, the empty bottles 10 are shifted laterally by side rails 13 and by means of a crossover plate 15, which bridges the gap between the conveyors 12, 14 in the region of the shifting movement, sufficiently far for them to have only a portion of their edges still standing on the first conveyor 12, while they have their opposite edge portion standing on the second conveyor 14. A bottom blower device is also integrated into the crossover plate.

The second conveyor 14 moves at a speed which is for example 20% higher than the first conveyor 12, so that the empty bottles 10 which are standing on both conveyors 12, 14 are rotated about their vertical axis. This gives the empty bottles 10 a tendency, while they are rotating, to drift towards the slower conveyor, i.e. the first conveyor 12. In order to prevent such a lateral drift or shifting of the empty bottles 10, a rail 16 is arranged above the first conveyor 12, stretching along the direction of transport. The position of the rail 16, angled to the direction of transport, is set in this case such that the separation from the edge of the first conveyor corresponds to about ⅙ of the diameter of the empty bottles 10, so that the empty bottles 10 stand on an edge region of this width of the first conveyor 12. Additionally, a rail 17 is also arranged above the second conveyor 14, since individual empty bottles 10 can occasionally drift towards the faster conveyor 14, as a result of an uneven bottom, for example.

The direction of transport and the rotation of the objects are shown by arrows. Side wall checking installations 20, 22, which consist in each case of a light source 26, which is of large area, and a CCD camera 28, are arranged at a distance from each other within which the empty bottles 10 rotate by 90° about their vertical axis. A two-stage side wall inspection, with intervening rotation of the bottles by 90°, is obviously sufficient only in the case of empty bottles made of transparent material, such as glass or plastic. The side wall checking installations check the empty bottles in the usual way for freedom from flaws, and for that reason will not be described in detail.

Within the gap remaining between the two conveyors 12, 14, light sources 30, 32, which are of large area, are provided, forming part of a bottom checking installation. The associated CCD cameras 31, 33 are located above the empty bottles 10. The CCD cameras, in a known way, take a picture of the bottom of the bottles through the mouth of the bottle, and this is subjected to checking. The two bottom checking installations and so also the associated light sources 30, 32 are likewise separated by a spacing in the direction of transport, within which the empty bottles 10 rotate through 90°, so that, overall, the entire bottom region is inspected. After the passage through the inspection device, the empty bottles 10 are again shifted back by side rails 13 and a crossover plate 15 completely onto the first conveyor 12.

FIGS. 3 and 4 show a checking device similar to that of FIGS. 1 and 2, in which, however, only a single-stage side wall check is undertaken. The side wall checking installation once again consists of a large-area light source 26 and a CCD camera. The light source 26 in this case, however, extends over a distance within which the empty bottles 10 perform a rotation by 90° about their vertical axis. This is the case for empty bottles or other objects made of transparent material. When the empty bottles or other objects consist of opaque material, or when labels extending around the entire bottle have to be checked, the light source 26 extends over a length within which the objects perform a complete rotation. In reality, a rotation of about 270° or even 220° is adequate for the purpose of inspecting the entire circumference of an empty bottle, when it is borne in mind that, for one thing, the camera in any case covers about 90° of the circumference of the empty bottle at any one time, and, for another, while the empty bottles 10 are moving past in front of the CCD camera 28 the field of view changes from one edge to the other edge of the wide-angle lens of the CCD camera 28. In this regard, it is essential that the CCD camera is arranged on the same side as the faster conveyor, i.e. the second conveyor 14, as is shown in FIG. 3.

In the exemplary embodiment of FIGS. 3 and 4, two bottom checking installations are again arranged at a distance from each other within which the empty bottles rotate by 90° or 270° about their vertical axis. In FIG. 4, however, only the light sources 30, 32 are again arranged under the empty bottles 10, and CCD cameras 31, 33, above the empty bottles 10.

An exemplary embodiment is shown in FIG. 5, in which the bottom checking is carried out in two increments, which follow closely on one another with a slight separation, within the crossover plate 15, which is arranged at the intake end of the inspection device. By means of the rail 16, the empty bottles 10 in this case are shifted sufficiently far towards the second conveyor 14 for them no longer to stand on the first conveyor 12 but rather only on the crossover plate 15 and the second conveyor 14. The first large-area light source 30 of the bottom checking installation is set up, with the first CCD camera, not portrayed, located vertically above it at the point where the empty bottles 10 are still standing with about 40% on the first conveyor 12 and 60% already standing on the crossover plate 15. In FIG. 5 the empty bottle 10a is located above the first light source 30. The second large-area light source 32 is arranged almost immediately afterwards, such that here the empty bottles 10 have about 60% of their under surface on the crossover plate 15 and about 40% on the second conveyor 14. In the exemplary embodiment depicted, the empty bottle 10b is located above the second light source 32. A CCD camera, not depicted, is also located above the second light source 32. Between the two light sources 30 and 32, and therefore between the two increments of the bottom checking, the objects 10 rotate only slightly because of their inertia and due to the support of first one then the other, opposite edge portion on the crossover plate 15, so that the two 60% regions of the bottom surface, which are covered by the first and second increments of the bottom checking, together amount to the entire bottom surface. The rail 17 swings back slightly towards the first conveyor 12, so that, after the second light source 32, the objects 10, after the bottom inspection and upon leaving the crossover plate 15, again stand with opposite edge portions on both conveyors 12, 14. Next, the side wall checking is carried out, in the way described in connection with FIGS. 1 and 2 or 3 and 4 respectively. In the exemplary embodiment depicted, similarly to FIGS. 3 and 4, a single-stage side wall check is carried out, for which a CCD camera 28 with a correspondingly wide field of view is used.

The inspection device can also be employed in the case of objects which are not rotationally symmetric, for example empty bottles with a square footprint. In order to achieve rotation of objects of this kind with essentially no lateral displacement of the centre of gravity, the rail is in this case formed to correspond to the curve which a corner line of such an object describes during rotation and simultaneous onward movement. The side wall checking installation can in this case again be formed in accordance with FIG. 1 or FIG. 3. The bottom checking is again located at a distance within which the empty bottles rotate by 90° or 270°, so that, in essence, the entire bottom region is checked.

What is claimed is:

1. A device for inspecting objects having a vertical axis, the device comprising:
    a first conveyor having a horizontal conveyor surface and running at a first speed;
    a second conveyor having a horizontal conveyor surface and running at a second speed that is faster than the first speed;
    wherein the first and the second conveyors speeds cause the objects to rotate about their vertical axis and wherein the first and the second conveyors are separated by a mutual lateral separation; and
    a bottom checking means provided below the first and second conveyors to inspect the rotating objects within the separation.

2. The device according to claim 1 wherein the objects rotate by about 90° or 270°, the device further comprising a second bottom checking means provided below the first and second conveyors to inspect the objects within the separation and wherein the first and second.

3. The device according to claim 1 further comprising a side wall checking installation, which features a light source and a recognition installation, between which the two conveyors are arranged.

4. The device according to claim 1 further comprising a rail for guiding the objects wherein the rail is arranged stretching in the direction of transport above the first conveyor, in such a way that the width of the region of the first conveyor on which the objects stand is about ⅓ of the diameter of the objects.

5. The device according to claim 4 wherein the rail is arranged so that the objects are shifted slightly towards the first conveyor.

6. The device according to one of claim 1 further comprising:
    a transparent crossover plate arranged between the first and second conveyors;
    rails which are laterally arranged above the first and second conveyors an extend in the direction of transport to guide the objects; and
    wherein the first and second bottom checking installations are arranged within the longitudinal extent of the crossover plate, and wherein the rails are arranged in such a way that the objects, in the region of one bottom checking installation stand with about 40% of their under surface on the first conveyor and with about 60% of their under surface on the crossover plate, and that, at the other bottom checking installation, they stand with about 40% of their under surface on the second conveyor and about 60% on the crossover plate.

7. The device according to claim 6 wherein the two bottom checking installations are arranged such a small distance apart that the two 60% regions of the object which are covered by the bottom inspection installations amount to the entire bottom surface of the objects.

8. The device according to claim 1 further comprising first and second rails which are laterally arranged above the first and second conveyors respectively, and extend in the direction of transport to guide the objects.

9. The device according to claim 8 wherein the rails are arranged so that the objects are shifted slightly towards the first conveyor.

10. The device according to claim 8 wherein the objects rotate between about 90° or 270°.

11. The device according to claim 8 further comprising a second bottom checking installation provided below the first and second conveyors to inspect the objects within the separation and wherein the first and second.

12. The device according to one of claim 11 further comprising:
    a transparent crossover plate arranged between the first and second conveyors;
    rails which are laterally arranged above the first and second conveyors an extend in the direction of transport to guide the objects; and
    wherein the first and second bottom checking installations are arranged within the longitudinal extent of the crossover plate, and wherein the rails are arranged in such a way that the objects, in the region of one bottom checking installation stand with about 40% of their under surface on the first conveyor and with about 60% of their under surface on the crossover plate, and that, at the other bottom checking installation, they stand with about 40% of their under surface on the second conveyor and about 60% on the crossover plate.

13. The device according to claim 12 wherein the two bottom checking installations are arranged such a small distance apart that the two 60% regions of the object which are covered by the bottom inspection installations amount to the entire bottom surface of the objects.

14. A method for inspecting objects having a vertical axis comprising the following steps:

- transporting objects by a conveyor means, which features a first and second conveyor running at different speeds and having an essentially horizontal conveyor surface for conveying the objects and at the same time rotating the objects about their vertical axis, wherein the first and second conveyors are separated by a mutual lateral separation; and
- inspecting the rotating objects by a bottom checking means within the distance separating the conveyors.

15. The method according to claim 14 further comprising the step of inspecting the objects by a side wall inspection installation while the objects are being rotated.

* * * * *